United States Patent

Maruyama et al.

[11] 4,010,280
[45] Mar. 1, 1977

[54] PHENOXYALKYLAMINE DERIVATIVES AND PREPARATION THEREOF

[75] Inventors: Isamu Maruyama, Minoo; Masaru Nakao; Kikuo Sasajima, both of Toyonaka; Shigeho Inaba, Takarazuka; Hisao Yamamoto, Nishinomiya, all of Japan

[73] Assignee: Sumitomo Chemical Company, Limited, Japan

[22] Filed: Sept. 27, 1974

[21] Appl. No.: 509,952

[30] Foreign Application Priority Data

Sept. 28, 1973 Japan .................. 48-109983

[52] U.S. Cl. .................. 424/316; 260/501.18; 260/501.19; 260/558 A; 260/558 S; 260/559 B; 260/570.5 S; 260/570.5 P; 260/570.7; 424/330

[51] Int. Cl.² .................. A01N 9/20; C07C 91/16; C07C 93/06

[58] Field of Search ..... 260/570.7, 501.18, 501.19; 424/316, 330

[56] References Cited

UNITED STATES PATENTS

| | | | |
|---|---|---|---|
| 2,547,365 | 4/1951 | Bock et al. .................. | 260/570.7 X |
| 2,599,001 | 6/1952 | Kerwin et al. .................. | 260/570.7 |
| 3,154,581 | 10/1964 | Dice .................. | 260/570.7 |
| 3,159,676 | 12/1964 | Spickett et al. ............ | 260/570.5 X |
| 3,663,712 | 5/1972 | Schmeling et al. ................. | 424/330 |

*Primary Examiner*—Robert V. Hines
*Attorney, Agent, or Firm*—Stewart and Kolasch, Ltd.

[57] ABSTRACT

A phenoxyalkylamine derivative of the formula:

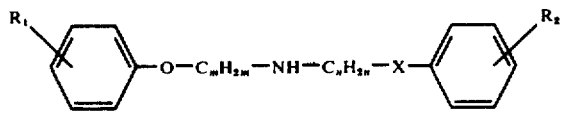

and its pharmaceutically acceptable salts, which are useful as neuroleptic agents and a process for their preparation by reacting a compound of the formula:

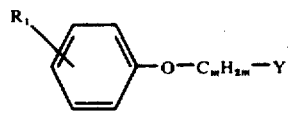

with a compound of the formula:

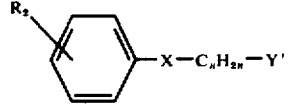

wherein $R_1$ and $R_2$ are each hydrogen, halogen, $C_1$–$C_7$ alkyl or $C_1$–$C_7$ alkoxy, X is oxygen, sulfur, sulfinyl or NR (in which R is hydrogen or $C_1$–$C_7$ alkyl), $m$ and $n$ are each an integer of 2, 3 or 4, and Y and Y' are each amino or halogen but they are different from each other.

6 Claims, No Drawings

PHENOXYALKYLAMINE DERIVATIVES AND PREPARATION THEREOF

The present invention relates to novel phenoxyalkylamine derivatives, and their preparation and use. More particularly, it relates to novel phenoxyalkylamine derivatives represented by the formula:

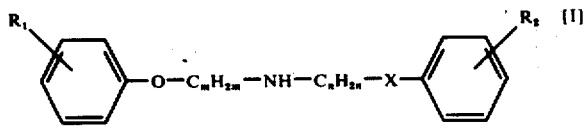

wherein $R_1$ and $R_2$ are each hydrogen, halogen, $C_1$–$C_7$ alkyl or $C_1$–$C_7$ alkoxy, X is oxygen, sulfur, sulfinyl or NR (in which R is hydrogen or $C_1$–$C_7$ alkyl), and $m$ and $n$ are each an integer of 2, 3, or 4, and their pharmaceutically acceptable salts, to pharmaceutical compositions comprising them with pharmaceutically acceptable carriers, and to a process for preparing them.

As used herein, the terms "$C_1$–$C_7$ alkyl" and "$C_1$–$C_7$ alkoxy" mean such groups containing from one to seven carbon atoms which can be either straight or branched. Thus, the $C_1$–$C_7$ alkyl group represents, for example, methyl, ethyl, n-propyl, isopropyl, n-butyl, isobutyl, n-hexyl or the like, and the $C_1$–$C_7$ alkoxy group represents, for example, methoxy, ethoxy, n-propoxy, isopropoxy, n-butoxy, isobutoxy, sec.-butoxy, n-pentoxy or the like. The term "halogen" includes all four halogens, i.e. iodine, bromine, chlorine and fluorine.

Each group of the formulas: —$C_mH_{2m}$— and —$C_nH_{2n}$— represents a straight or branched chain alkylene group having up to four carbon atoms and includes, for example, ethylene, trimethylene, 1-methyltrimethylene, 2-methyltrimethylene and tetramethylene.

The phenoxyalkylamine derivatives [I] form pharmaceutically acceptable salts with a variety of inorganic and organic acids such as sulfuric, phosphoric, hydrochloric, hydrobromic, nitric, oxalic, malonic, succinic, lactic, tartaric, maleic, fumaric, formic, acetic, salicylic and p-toluenesulfonic acids.

The phenoxyalkylamine derivatives [I] show neuroleptic activity and antihypertensive activity, and they are useful as neuroleptic agents and antihypertensive agents.

Among the phenoxyalkylamine derivatives [I], preferred are those represented by the formula:

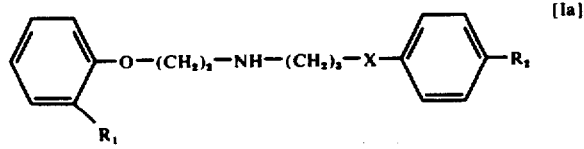

wherein $R_1$, $R_2$ and X are each as defined above. Especially, the marked neuroleptic activity of the phenoxyalkylamine derivatives of the formula:

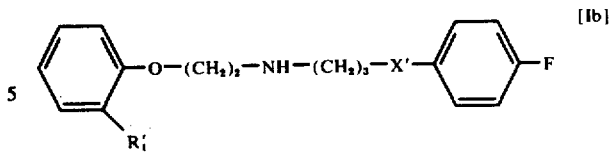

wherein $R_1'$ is $C_1$–$C_3$ alkoxy and $X'$ is oxygen, sulfur or NR (in which R is as defined above) is notable.

The phenoxyalkylamine derivatives [I] and their pharmaceutically acceptable salts can be administered orally in conventional dosage forms such as a tablet, capsule, solution, suspension, elixir and the like.

A typical tablet may be constituted by from 1 to 20 percent by weight of a binder (e.g. tragacanth), from 1 to 20 percent by weight of a lubricant (e.g. talcum, magnesium stearate), an average dose of the active ingredient and q.s. 100 percent by weight of a filler (e.g. lactose). The usual oral dosage of the active ingredient may be from 1 to 1000 mg per day.

Accordingly, a basic object of the present invention is to provide novel phenoxyalkylamine derivatives [I] and their pharmaceutically acceptable salts, which have excellent pharmacological properties. Another object of this invention is to provide processes for producing such novel and useful phenoxyalkylamine derivatives [I] and their salts. A further object of the invention is to provide pharmaceutical compositions comprising such novel and useful phenoxyalkylamine derivatives [I] or their salts. These and other objects of the invention will be apparent from the foregoing and subsequent descriptions.

According to the present invention, the novel phenoxyalkylamine derivative [I] can be prepared by reacting a compound of the formula:

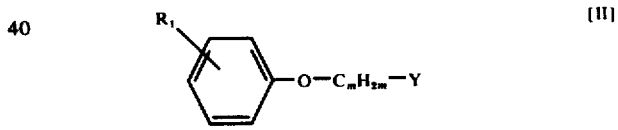

wherein Y is amino or halogen and $R_1$ and $m$ are each as defined above with a compound of the formula:

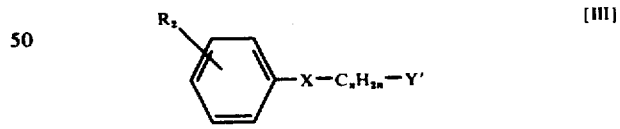

wherein $Y'$ is halogen when Y is amino or amino when Y is halogen and $R_2$, X and $n$ are each as defined above.

The reaction may be carried out in the absence or presence of an acid acceptor in an inert organic solvent (e.g. benzene, toluene, xylene, dimethylformamide, pyridine, methanol, ethanol) at a temperature from about room temperature to the boiling temperature of the solvent used. Suitable acid acceptors include sodium carbonate, potassium carbonate, sodium bicarbonate, potassium bicarbonate, sodium hydroxide, potassium hydroxide, sodium hydride, potassium hydride, triethylamine, etc.

The phenoxyalkylamine derivative of the formula:

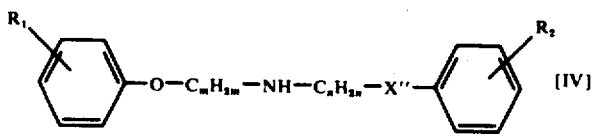

wherein X" is oxygen, sulfur or NR (in which R is as defined above) and $R_1$, $R_2$, m and n are each as defined above can be also prepared by reducing a compound of the formula:

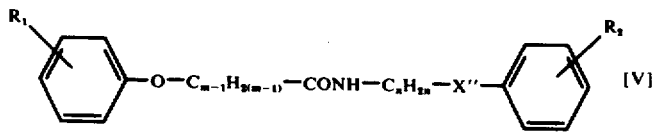

wherein $R_1$, $R_2$, X", m and n are each as defined above or a compound of the formula:

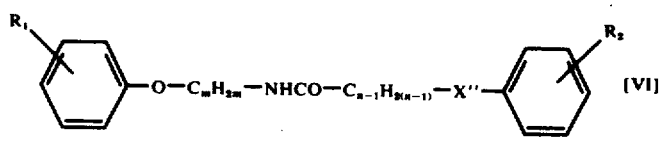

wherein $R_1$, $R_2$, X", m and n are each as defined above with a reducing agent.

The phenoxyalkylamine derivative of the formula:

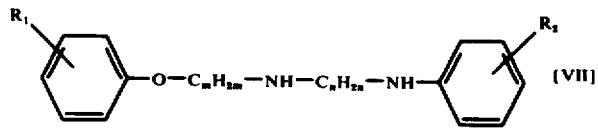

wherein $R_1$, $R_2$, m and n are each as defined above can be also prepared by reducing a compound of the formula:

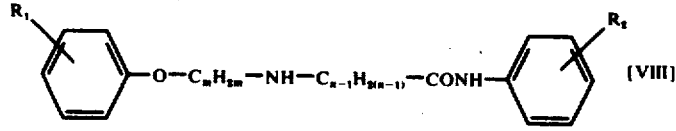

wherein $R_1$, $R_2$, m and n are each as defined above with a reducing agent.

Preferred examples of the reducing agent are metal hydride complexes such as lithium aluminum hydride, lithium aluminum hydride-aluminum chloride, sodium borohydride-aluminum chloride and sodium borohydride-boron trifluoride. The reaction is usually effected in the presence of a solvent (e.g. water, ethanol, ether, tetrahydrofuran, dioxane, N-ethylmorpholine) at a wide range of temperature, for instance while cooling, at room temperature or under an elevated temperature.

The said compounds [V], [VI] and [VIII] may be produced by conventional procedures, for instance, as shown in the following reaction scheme:

-continued
Scheme 1
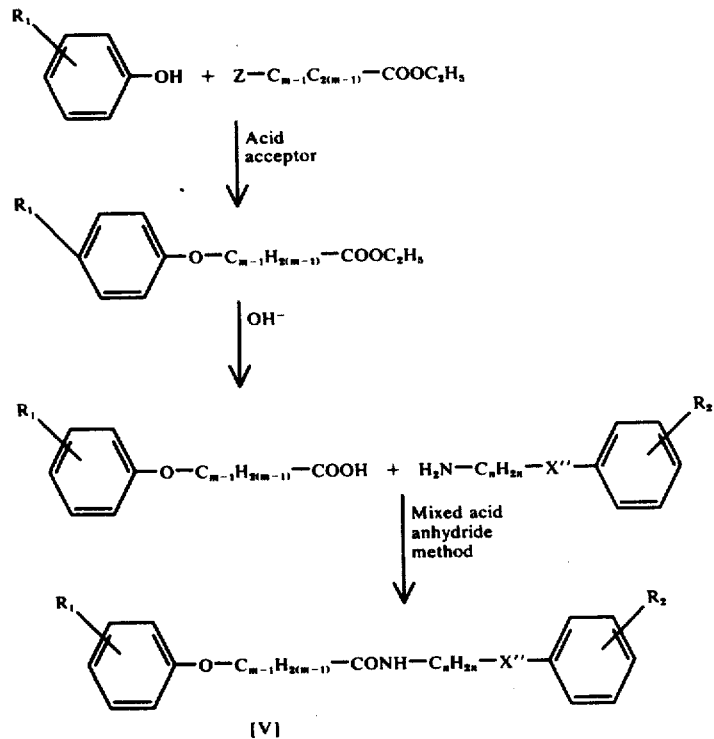
Scheme 2
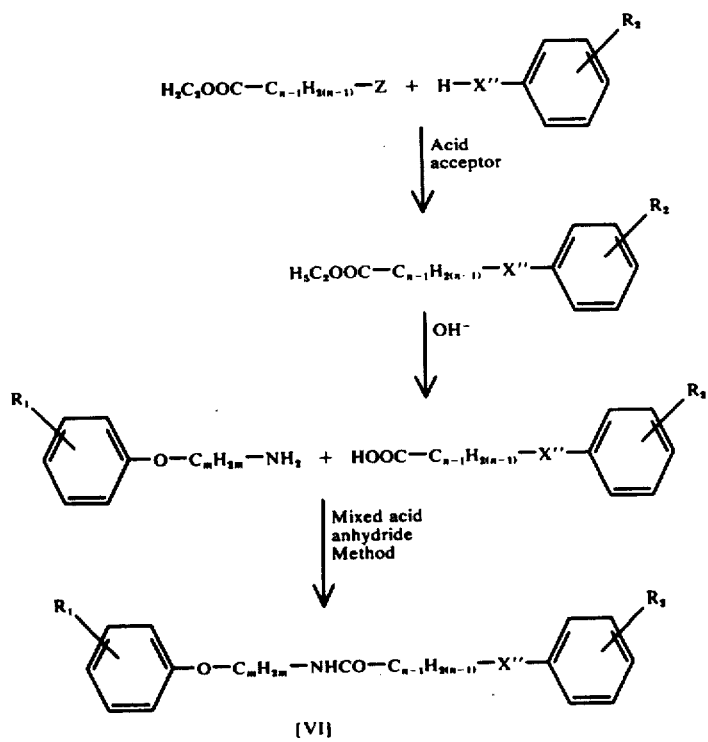

Scheme 3

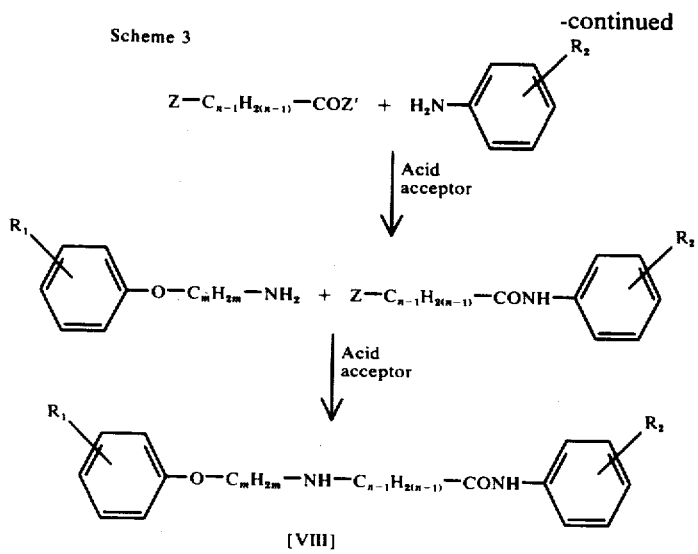

[VIII]

In the above scheme, Z and Z' each represent halogen and $R_1$, $R_2$, $X''$, $m$ and $n$ are each as defined above.

When the thus obtained phenoxyalkylamine derivative [I] is in a free base form, it may be converted into the acid-addition salt by interaction with an acid. In like manner, the free base can be regenerated from the acid-addition salt in a conventional manner, for instance, by treating with a strong base (e.g. alkali metal hydroxide, alkali metal carbonate, alkali metal bicarbonate). The base thus regenerated can then be interacted with an acid to give the corresponding acid-addition salt.

Examples of the phenoxyalkylamine derivatives [I] obtainable by the present invention are as follows:

N-{2-(2-Ethoxyphenoxy)ethyl}-3-(4-fluorophenoxy)-propylamine;
N-{2-(2-Methoxyphenoxy)ethyl}-3-(4-fluorophenoxy)propylamine;
N-{2-(2-n-Propoxyphenoxy)ethyl}-3-(4-fluorophenoxy)propylamine;
N-{2-(2-Isopropoxyphenoxy)ethyl}-3-(4-fluorophenoxy)propylamine;
N-{2-(2-Chlorophenoxy)ethyl}-3-(4-fluorophenoxy)-propylamine;
N-{2-(o-Tolyloxy)ethyl}-3-(4-fluorophenoxy)propylamine;
N-{2-(2-Ethoxyphenoxy)ethyl}-3-(p-tolyloxy)propylamine;
N-{2-(2-Ethoxyphenoxy)ethyl}-3-(4-methoxyphenoxy)propylamine;
N-{2-(2-Ethoxyphenoxy)ethyl}-3-(4-fluorophenylthio)propylamine;
N-{2-(2-Methoxyphenoxy)ethyl}-3-(4-fluorophenylthio)propylamine;
N-{2-n-Propoxyphenoxy)ethyl}-3-(4-fluorophenylthio)propylamine;
N-{2-(2-Isopropoxyphenoxy)ethyl}-3-(4-fluorophenylthio)propylamine;
N-{2-(2-Chlorophenoxy)ethyl}-3-(4-fluorophenylthio)propylamine;
N-{2-(o-Tolyloxy)ethyl}-3-(4-fluorophenylthio)-propylamine;
N-{2-(2-Ethoxyphenoxy)ethyl}-3-(p-tolylthio)-propylamine;
N-{2-(2-Ethoxyphenoxy)ethyl}-3-(4-methoxyphenylthio)propylamine;
N-{2-(2-Ethoxyphenoxy)ethyl}-3-(4-fluorophenylsulfinyl)propylamine;
N-{2-(2-Ethoxyphenoxy)ethyl}-3-(4-fluoroanilino)-propylamine;
N-{2-(2-Methoxyphenoxy)ethyl}-3-(4-fluoroanilino)-propylamine;
N-{2-(2-n-Propoxyphenoxy)ethyl}-3-(4-fluoroanilino)propylamine;
N-{2-(2-Isopropoxyphenoxy)ethyl}-3-(4-fluoroanilino)propylamine;
N-{2-(2-Chlorophenoxy)ethyl}-3-(4-fluoroanilino)-propylamine;
N-{2-(o-Tolyloxy)ethyl}-3-(4-fluoroanilino)propylamine;
N-{2-(2-Ethoxyphenoxy)ethyl}-3-(4-p-anisidino)-propylamine;
N-{2-(2-Ethoxyphenoxy)ethyl}-3-(p-toluidino)-propylamine;
N-{2-(2-Ethoxyphenoxy)ethyl}-3-(N-ethyl-p-fluoroanilino)propylamine, etc.

The present invention is further disclosed in the following examples of more preferred embodiments thereof, which are presented for the purpose of illustration, and the examples not intended to limit the scope of the invention.

EXAMPLE 1

A mixture of 1.9 g of 1-chloro-3-(4-fluorophenoxy)-propane, 1.8 g of 2-(2-ethoxyphenoxy)ethylamine, 0.53 g of sodium carbonate and 60 ml of dimethylformamide was heated at 80°–90° C for 15 hours. After cooling, the reaction mixture was poured into water and extracted with benzene. The extract was washed with water and dried over sodium sulfate and evaporated under reduced pressure. The oily residue was dissolved in ether and treated with ethanolic hydrogen chloride under cooling. The precipitate was collected by filtration and dried to give N-{2-(2-ethoxyphenoxy)ethyl}-3-(4-fluorophenoxy)propylamine hydrochloride, M.P. 78°–82° C. Recrystallization from ethanol-benzene gave white crystals, M.P. 84°–86° C.

The following compounds were obtained in the same manner as above:

N-{2-(2-Ethoxyphenoxy)ethyl}-3-(4-fluorophenylthio)propylamine hydrochloride, M.P. 79°–80° C;

N-{2-(2-Ethoxyphenoxy)ethyl}-3-(4-fluorophenylsulfinyl)propylamine, M.P. 60°–61° C;

N-{2-(o-Tolyloxy)ethyl}-3-(4-fluorophenoxy)propylamine hydrochloride, M.P. 132°–133° C (decomp.);

N-{2-(2-Ethoxyphenoxy)ethyl}-3-(4-fluoroanilino)propylamine hydrogen oxalate, M.P. 218°–218.5° C (decomp.);

N-{2-(2-Ethoxyphenoxy)ethyl}-3-(N-ethyl-4-fluoroanilino)propylamine hydrogen oxalate, M.P. 173°–174° C (decomp.).

EXAMPLE 2

To a mixture of 1.4 g of lithium aluminum hydride and 50 ml of tetrahydrofuran, there was added dropwise a solution of 6.15 g of N-{2-(2-ethoxyphenoxy)ethyl}-3-(p-fluorophenylthio)propionamide in 20 ml of tetrahydrofuran. The mixture was refluxed for 3 hours. To the reaction mixture cooled in ice, there were gradually added water and benzene. The organic layer was separated, washed with water, dried over sodium sulfate and evaporated under reduced pressure. The oily residue was dissolved in ether and treated with ethanolic hydrogen chloride under cooling. The precipitate was collected by filtration and dried to give N-{2-(2-ethoxyphenoxy)ethyl}-3-(4-fluorophenylthio)propylamine hydrochloride, M.P. 73°–75° C. Recrystallization from benzene gave white crystals, M.P. 79°–80° C.

EXAMPLE 3

To a mixture of 0.35 g of lithium aluminum hydride and 15 ml of tetrahydrofuran, there was added dropwise a solution of 2.05 g of 3-{2-(2-ethoxyphenoxy)ethylamino}-p-fluoropropionanilide in 20 ml of tetrahydrofuran. Then, the resulting mixture was refluxed for 3 hours. To the reaction mixture cooled in ice, there were gradually added water and benzene. The organic layer was separated, dried over sodium sulfate and evaporated under reduced pressure. The oily residue was dissolved in isopropanol, and a warm solution of 0.8 g of oxalic acid in 10 ml of isopropanol was added thereto. After cooling, the precipitate was collected by filtration and dried to give N-{2-(2-ethoxyphenoxy)ethyl}-3-(4-fluoroanilino)propylamine hydrogen oxalate, M.P. 193°–196° C (decomp.). Recrystallization from methanol gave white crystals, M.P. 218°–219° C (decomp.).

What is claimed is:

1. A compound selected from the group consisting of

N-{2-(2-ethoxyphenoxy)ethyl}-3-(4-fluorophenoxy)propylamine,

N-{2-(2-ethoxyphenoxy)ethyl}-3-(4-fluorophenylthio)propylamine,

N-{2-(2-ethoxyphenoxy)ethyl}-3-(4-fluoroanilino)propylamine,

N-{2-(2-ethoxyphenoxy)ethyl}-3-(N-ethyl-4-fluoroanilino)propylamine and pharmaceutically acceptable salts thereof.

2. A pharmaceutical composition comprising an effective neuroleptic or antihypertensive amount of the compound of claim 1, and a pharmaceutically acceptable carrier.

3. N-{2-(2-Ethoxyphenoxy)ethyl}-3-(4-fluorophenoxy)propylamine and pharmaceutically acceptable salts thereof.

4. N-{2-(2-Ethoxyphenoxy)ethyl}-3-(4-fluorophenylthio)propylamine and pharmaceutically acceptable salts thereof.

5. N-{2-(2-(2-Ethoxyphenoxy)ethyl}-3-(4-fluoroanilino)propylamine and pharmaceutically acceptable salts thereof.

6. N-{2-(2-Ethoxyphenoxy)ethyl}-3-(N-ethyl-4-fluoroanilino)propylamine and pharmaceutically acceptable salts thereof.

* * * * *